US010479991B2

(12) United States Patent
Jiang et al.

(10) Patent No.: US 10,479,991 B2
(45) Date of Patent: Nov. 19, 2019

(54) METHOD AND REAGENT FOR CONSTRUCTING NUCLEIC ACID DOUBLE-LINKER SINGLE-STRAND CYCLICAL LIBRARY

(71) Applicants: BGI SHENZHEN, Shenzhen (CN); BGI SHENZHEN CO., LIMITED, Shenzhen (CN)

(72) Inventors: Yuan Jiang, Shenzhen (CN); Qiaoling Li, Shenzhen (CN); Andrei Alexeev, Woodland, CA (US); Evan Hurowitz, Mountain View, CA (US); Xia Zhao, Shenzhen (CN); Tong Wang, Shenzhen (CN); Chao Dong, Shenzhen (CN); Dong Li, Shenzhen (CN); Radoje Drmanac, Los Altos Hills, CA (US); Wenwei Zhang, Shenzhen (CN); Hui Jiang, Shenzhen (CN)

(73) Assignee: MGI TECH CO., LTD, Shenzhen, Guangdong (CN)

( * ) Notice: Subject to any disclaimer, the term of this patent is extended or adjusted under 35 U.S.C. 154(b) by 0 days.

(21) Appl. No.: 15/529,881

(22) PCT Filed: Nov. 26, 2014

(86) PCT No.: PCT/CN2014/092296
  § 371 (c)(1),
  (2) Date: May 25, 2017

(87) PCT Pub. No.: WO2016/082129
  PCT Pub. Date: Jun. 2, 2016

(65) Prior Publication Data
  US 2017/0355981 A1    Dec. 14, 2017

(51) Int. Cl.
  C12N 15/10    (2006.01)
  C40B 50/18    (2006.01)
  B01J 19/00    (2006.01)
  C40B 50/06    (2006.01)

(52) U.S. Cl.
  CPC ...... C12N 15/1068 (2013.01); B01J 19/0046 (2013.01); C12N 15/10 (2013.01); C12N 15/1093 (2013.01); C40B 50/18 (2013.01); B01J 2219/00596 (2013.01); B01J 2219/00722 (2013.01); C40B 50/06 (2013.01)

(58) Field of Classification Search
  CPC .................. C12N 15/10; B01J 19/00
  See application file for complete search history.

(56) References Cited

U.S. PATENT DOCUMENTS

| 2009/0181861 | A1 | 7/2009 | Li et al. |
| 2013/0164757 | A1 | 6/2013 | Mizuno et al. |
| 2014/0329697 | A1 | 11/2014 | Gao et al. |
| 2017/0355981 | A1* | 12/2017 | Jiang .................. C12N 15/1068 |

FOREIGN PATENT DOCUMENTS

| CN | 102016068 A | 4/2011 | |
| CN | 102534811 A | 7/2012 | |
| CN | 102628079 A | 8/2012 | |
| CN | 103103624 A | 5/2013 | |
| CN | 103119162 A | 5/2013 | |
| CN | 103290106 A | * 9/2013 | ........... C12Q 1/6827 |
| CN | 103290106 A | 9/2013 | |
| CN | 103806111 A | 5/2014 | |
| EP | 2565279 A1 | * 3/2013 | ........... C12Q 1/6827 |
| WO | 0120039 A2 | 3/2001 | |
| WO | WO-2010086622 A1 | * 8/2010 | ........... C12Q 1/6869 |

OTHER PUBLICATIONS

Zohar et al., Labeling DNA for Single-Molecule Experiments: Methods of Labeling Internal Specific Sequences on Double-Stranded DNA, Nanoscale, 2011, 3, 3027-3039. (Year: 2011).*
Head et al., Library Construction for Next-Generation Sequencing: Overviews and Challenges, Author Manuscript, HHS Public Access, 2014, 1-31. (Year: 2014).*
Anderson et al., Next Generation DNA Sequencing and the Future of Genomic Medicine, Genes, 2010, 1, 36-69. (Year: 2010).*
Hebelstrup et al., UCE: A Uracil Excision (USER)-Based Toolbox for Transformation of Cereals, Plant Methods, 2010, 6(15), 1-10. (Year: 2010).*
U.S. Appl. No. 15/529,967, filed May 25, 2017, Jiang et al.
International Search Report for PCT /CN2014/092296, dated Aug. 20, 2015, and its English translation provided by WIPO.
Written Opinion of the International Search Authority for PCT /CN2014/092296, dated Aug. 20, 2015, and its English translation provided by Bing.Com Microsoft Translator.
(Continued)

Primary Examiner — Amy M Bunker
(74) Attorney, Agent, or Firm — Ladas & Parry, LLP

(57) ABSTRACT

A method and reagent for constructing a nucleic acid double-linker single-strand cyclic library. The method comprises: breaking a nucleic acid into nucleic acid fragments; connecting a first linker sequence; producing by amplification a first product provided with the first linker sequence at either end, where a U nucleobase site is provided on primer sequences and a nicking enzyme recognition sequence is either provided or not provided on same, and a first affinity tag is provided on one of the primer sequences; using USER enzyme to cleave the first product; cyclizing the cleaved first product; treating the cyclization product with either a phosphatase or a nicking enzyme; using a solid-phase vector for combination with a cyclized molecule; performing a restrictive gap translation reaction; removing by digestion any portion that did not undergo the restrictive gap translation reaction; connecting a second linker sequence; producing by amplification a second product provided with the second linker sequence at either end; denaturing the second product, and cyclizing a single-strand nucleic acid molecule. The method allows an increase in the length of library insert fragments, a simplified library construction process, reduced library construction time, and reduced library construction costs.

9 Claims, 6 Drawing Sheets
Specification includes a Sequence Listing.

(56) References Cited

OTHER PUBLICATIONS

International Search Report for PCT/CN2014/092297, dated Aug. 26, 2015, and its English translation provided by WIPO.
Written Opinion of the International Search Authority for PCT/CN2014/092297, dated Aug. 26, 2015, and its English translation provided by WIPO.
PCT International Preliminary Report on Patentability (Chapter I) with Written Opinion from PCT/CN2014/092296 dated May 30, 2017, and its English translation from WIPO.
English translation from WIPO for the Written Opinion from PCT/CN2014/092296 dated Aug. 20, 2015.

* cited by examiner

SEQUENCE LISTING

<160> NUMBER OF SEQ ID NOS: 10

<210> SEQ ID NO 1
<211> LENGTH: 45
<212> TYPE: DNA
<213> ORGANISM: Artificial Sequence
<220> FEATURE:
<223> OTHER INFORMATION: Synthetic Sequence
<220> FEATURE:
<221> NAME/KEY: phosphorylation modification
<222> LOCATION: (1)..(1)

<400> SEQUENCE: 1
aagctgaggg tactgtgtca taaatagcac gagacgttct cgact                45

<210> SEQ ID NO 2
<211> LENGTH: 12
<212> TYPE: DNA
<213> ORGANISM: Artificial Sequence
<220> FEATURE:
<223> OTHER INFORMATION: Synthetic Sequence
<220> FEATURE:
<221> NAME/KEY: Uracil
<222> LOCATION: (6)..(6)
<220> FEATURE:
<221> NAME/KEY: dideoxy modification
<222> LOCATION: (12)..(12)

<400> SEQUENCE: 2
taccctcagc tt                                                    12

<210> SEQ ID NO 3
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: Uracil
<222> LOCATION: (12)..(12)

<400> SEQUENCE: 3
acgttctcga ctcctcagct t                                          21

<210> SEQ ID NO 4
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: Uracil
<222> LOCATION: (12)..(12)
<220> FEATURE:
<221> NAME/KEY: biotin modification
<222> LOCATION: (17)..(17)

<400> SEQUENCE: 4
agtcgagaac gtctcgtgct                                            20

<210> SEQ ID NO 5
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: Uracil
<222> LOCATION: (12)..(12)

```
<400> SEQUENCE: 5
acgttctcga ctcctcagct t                                            21

<210> SEQ ID NO 6
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 6
agtcggaggc caagcgtgct taggacat                                     28

<210> SEQ ID NO 7
<211> LENGTH: 31
<212> TYPE: DNA
<213> ORGANISM: Artificial Sequence
<220> FEATURE:
<223> OTHER INFORMATION: Synthetic Sequence
<220> FEATURE:
<221> NAME/KEY: Uracil
<222> LOCATION: (12)..(12)

<400> SEQUENCE: 7
gtcctaagca ctgtagtgta cgatccgact t                                 31

<210> SEQ ID NO 8
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: biotin modification
<222> LOCATION: (1)..(1)

<400> SEQUENCE: 8
atgtcctaag cacgcttggc c                                            21

<210> SEQ ID NO 9
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 9
gtagtgtacg atccgactt                                               19

<210> SEQ ID NO 10
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 10
atcgtacact acatgtccta agca                                         24
```

METHOD AND REAGENT FOR CONSTRUCTING NUCLEIC ACID DOUBLE-LINKER SINGLE-STRAND CYCLICAL LIBRARY

CROSS REFERENCE TO RELATED APPLICATION

The present application is the U.S. national phase of PCT Application PCT/CN2014/092296 filed on Nov. 26, 2014, the disclosure of which is incorporated herein by reference in its entirety.

TECHNICAL FIELD

The present invention relates to the field of molecular biology, particularly to a method and a reagent for constructing a library of single-stranded cyclic nucleic acid fragments having double adaptors.

BACKGROUND OF THE INVENTION

Currently, high-throughput sequencing is one of the important research means in molecular biology, medical diagnosis, among other fields. Ever since the birth of the high-throughput second-generation sequencing technologies, rapid developments have been achieved in sequencing technologies. The sequencing cost in the second-generation sequencing has decreased by several orders of magnitude in comparison to the expensive sequencing cost in the past, and the sequencing time has been greatly shortened. Now, the emergence of the third-generation sequencer makes the competition of the sequencing markets even more intense and the development even more rapid. Therefore, every sequencing company or research group has to seek to reduce sequencing cost, shorten procedure time and increase result accuracy in order to take the lead in competition.

Among the second-generation sequencing platforms, a sequencing platform with a high precision and a high sequencing through-put, developed by Complete Genomics Corporation (CG), has a data accuracy of up to 99.9998%, providing accurate gene information for cancer research, detection of low-frequency mutations, and personal genome sequencing. However, the procedure time of library construction associated with the CG platform is too long, the cost of library construction is high, and the library insert fragments are short, limiting subsequent data generation and analysis. This will not only affect the progress of scientific research projects, but also hinder the use and development of the CG platform on a large scale and in wide areas. The library construction process must be optimized, the library construction time shortened, the library length increased and the cost lowered in order for the CG platform to maintain competitive advantage in the intense competitions at present. In the conventional library construction procedure with the CG platform, the steps from double strand cyclization to single strand cyclization at last are rather tedious. The library construction procedure mainly includes 12 steps: enzyme digestion of cyclic DNA, dephosphorylation, end repairing, ligation of 3' end adaptor, ligation of 5' end adaptor, gap translation, polymerase chain reaction, single strand separation, cyclization, among other steps, and purification using magnetic beads needs to be performed following each enzymatic reaction. Such a procedure is long and costly. The library insert fragments produced by enzyme digestion are only 26 bp. This is not only unfavorable to the application of the CG platform on a large scale, but also inconsistent with the requirements of CG next-generation sequencing platforms with respect to fragments.

SUMMARY OF THE INVENTION

The present invention provides a method and a reagent for constructing a library of single-stranded cyclic nucleic acid fragments having double adaptors. The method enables to increase the length of library insert fragments, simplify the library construction procedure, shorten the library construction time and lower the library construction cost.

In a first aspect of the present invention, there is provided a method for constructing a library of single-stranded cyclic nucleic acid fragments having double adaptors, comprising the following steps:

disrupting a nucleic acid into nucleic acid fragments for library construction;

ligating a first adaptor sequence to both ends of the nucleic acid fragments;

performing a first PCR amplification to obtain first products having the first adaptor sequence at both ends, wherein the primer sequences used in the first PCR have a U base site and have or do not have a nickase recognition sequence, and one of the primers has a first affinity label;

digesting the first products with a USER enzyme to generate sticky ends and generate or do not generate a gap;

cyclizing the digested first products to generate cyclic nucleic acid molecules;

treating the cyclic nucleic acid molecules having a gap on both strands with a dephosphorylase, or treating the cyclic nucleic acid molecules having a nickase recognition sequence on one strand and a gap on the other strand or having a nickase recognition sequence but not a gap on both strands with a nickase to generate a nick;

allowing a solid-phase carrier harboring a second affinity label to bind to the cyclic nucleic acid molecules;

initiating controlled gap translation reaction from the nick and/or gap by using the cyclic nucleic acid molecules bound to the solid-phase carrier as template;

digesting and removing the portion of the respective cyclic nucleic acid molecules that does not undergo the controlled gap translation reaction to obtain linear nucleic acid molecules;

ligating a second adaptor sequence to both ends of the linear nucleic acid molecules;

performing a second PCR amplification to obtain second products having the second adaptor sequence at both ends; and denaturing the second products to obtain single-stranded nucleic acid molecules, and cyclizing one of the single-stranded nucleic acid molecules with a mediating sequence complementary to both ends of the single-stranded nucleic acid molecule to obtain the library of single-stranded cyclic nucleic acid fragments having double adaptors.

In a preferred embodiment of the present invention, the first affinity label is a biotin label; and the second affinity label is a streptavidin label.

In a preferred embodiment of the present invention, the first adaptor sequence comprises a first 5' adaptor sequence and a first 3' L-type adaptor sequence that respectively ligate to the 3' end and the 5' end of each strand of the fragments; the first 5' adaptor sequence comprises a 5'-end-phosphorylated long strand and a complementary short strand, the short strand having dideoxy modification at the 3' end, and the short strand comprising a U base site; and a portion of the first 3' L-type adaptor sequence which is adjacent to the ligated fragment is complementary to part of the bases of the first 5' adaptor sequence; and said ligating a first adaptor sequence to both ends of the nucleic acid fragments specifically comprises:

dephosphorylating the nucleic acid fragments;

subjecting the dephosphorylated nucleic acid fragments to end repairing;

ligating the first 5' adaptor sequence to the 3' end of each strand of the nucleic acid fragments;

digesting the U base site of the short strand of the first 5' adaptor sequence with a USER enzyme;

phosphorylating the USER enzyme-digested nucleic acid fragments; and ligating the first 3' L-type adaptor sequence to the 5' end of each strand of the phosphorylated nucleic acid fragments.

In a preferred embodiment of the present invention, each of the primer sequences used in the first PCR has a U base site and a nickase recognition sequence; and after digesting the U base site with the USER enzyme, sticky ends are formed at both ends of the nucleic acid fragments, and cyclization occurs due to the complementarity of the sticky ends, generating cyclized nucleic acid molecules; then a nickase is used to digest the nickase recognition sequence to generate a nick.

In a preferred embodiment of the present invention, one of the primer sequences used in the first PCR has two U base sites, while the other primer sequence has a U base site; and after digesting the U base sites with the USER enzyme, sticky ends are formed at both ends of the nucleic acid fragments, and cyclization occurs due to the complementarity of the sticky ends, generating cyclized nucleic acid molecules.

In a preferred embodiment of the present invention, following cyclizing the digested first products, the method further comprises:digesting the nucleic acid molecules that are not cyclized.

In a preferred embodiment of the present invention, in the controlled gap translation reaction, the length of the gap translation fragments generated is controlled by controlling at least one factor selected from the group consisting of the molar ratio of dNTPs to the nucleic acid molecules as template, the enzymatic reaction temperature and the enzymatic reaction time.

In a preferred embodiment of the present invention, said digesting and removing the portion of the respective cyclic nucleic acid molecules that does not undergo the controlled gap translation reaction specifically comprises:first degrading the cyclic nucleic acid molecules with a double strand exonuclease until the gaps at both ends meet; and then degrading the resulting single strands with a single strand exonuclease; or directly excising the portion of the respective cyclic nucleic acid molecules that does not undergo the controlled gap translation reaction with an endonuclease.

In a preferred embodiment of the present invention, the second adaptor sequence is a bubble-type adaptor sequence, comprising two base sequences which are complementary to each other in terminal portions but not complementary to each other in a middle portion, thus forming a bubble shape in the middle portion; the middle portion harbors a U base site, and one of the strands of the bubble-type adaptor sequence has an overhanging T base at the 5' end; and said ligating a second adaptor sequence to both ends of the linear nucleic acid molecules specifically comprises:

subjecting the linear nucleic acid molecules to end repairing and to a reaction of adding A base to the 3' end;

ligating a bubble-type adaptor sequence to each end of the linear nucleic acid molecules by means of pairing of the T base with the A base; and digesting the U base site in the middle portion by using a USER enzyme.

In a preferred embodiment of the present invention, following cyclizing the single-stranded nucleic acid molecules, the method further comprises: digesting the single-stranded nucleic acid molecules that are not cyclized.

According to a second aspect of the present invention, there is provided a reagent for constructing a library of single-stranded cyclic nucleic acid fragments having double adaptors, comprising the following components:

a first adaptor sequence, which comprises a first 5' adaptor sequence and a first 3' L-type adaptor sequence that respectively ligate to the 3' end and the 5' end of each strand of the fragments, wherein the first 5' adaptor sequence comprises a 5'-end-phosphorylated long strand and a complementary short strand, the short strand having dideoxy modification at the 3' end, and the short strand comprising a U base site; and a portion of the first 3' L-type adaptor sequence which is adjacent to the ligated fragment is complementary to part of the bases of the first 5' adaptor sequence;

primers for a first PCR, which have a U base site and have or do not have a nickase recognition sequence and one of which has a first affinity label, and which are used to obtain first products having the first adaptor sequence at both ends by the first PCR amplification;

a USER enzyme, which is used for digesting the first products to generate sticky ends and generate or do not generate a gap;

a cyclase, which is used for cyclizing the digested first products to generate cyclic nucleic acid molecules;

dephosphorylase, which is used for dephosphorylating the cyclic nucleic acid molecules having a gap on both strands, or a nickase, which is used for digesting the cyclic nucleic acid molecules having a nickase recognition sequence on one strand and a gap on the other strand or having a nickase recognition sequence but not a gap on both strands to generate a nick;

a solid-phase carrier harboring a second affinity label, which is used for binding to the cyclic nucleic acid molecules;

gap translation reaction components, which are used for initiating controlled gap translation reaction from the nick and/or gap by using the cyclic nucleic acid molecules bound to the solid-phase carrier as template;

a digestive enzyme, which is used for digesting and removing the portion of the respective cyclic nucleic acid molecules that does not undergo the controlled gap translation reaction to obtain linear nucleic acid molecules;

a second adaptor sequence, which is a bubble-type adaptor sequence comprising two base sequences which are complementary to each other in terminal portions but not complementary to each other in a middle portion, thus forming a bubble shape in the middle portion; the middle portion harboring a U base site, and one of the strands of the bubble-type adaptor sequence having an overhanging T base at the 5' end;

primers for a second PCR, which are used for performing the second PCR amplification to obtain second products having the second adaptor sequence at both ends; and a mediating sequence, which is complementary to both ends of one of the single-stranded nucleic acid molecules following denaturing the second products, and which is used for cyclizing the single-stranded nucleic acid molecule to obtain the library of single-stranded cyclic nucleic acid fragments having double adaptors.

In a preferred embodiment of the present invention, the first affinity label is a biotin label; and the second affinity label is a streptavidin label.

The method for constructing a library of single-stranded cyclic nucleic acid fragments having double adaptors according to the present invention combines the controlled gap translation reaction with the enzymatic reactions performed on magnetic beads. In the controlled gap translation reaction, a novel nickase site is used in place of the III class endonuclease site in the conventional method, and controlled nucleic acid strand extension is initiated from the gap or nick, achieving an increase in the length of the library insert fragments. Moreover, after binding the cyclic nucleic acid molecules to magnetic beads, the enzymatic reactions are allowed to proceed on the magnetic beads by directly adding the enzymatic reaction solutions, without the need to elute the nucleic acids. Such on-beads reactions are conducted until the step of eluting single strands, without the need for a plurality of operations of binding to and eluting from magnetic beads among the steps involved, which shortens the time required for library construction and also saves the cost associated with repeated addition of new magnetic beads.

DETAILED DESCRIPTION OF THE INVENTION

The present invention is described in further detail below by reference to particular embodiments. Unless otherwise stated, the techniques used in the following embodiments are all conventional techniques known to a person skilled in the art, and the instruments, equipments and reagents used are all publicly available, e.g. commercially available, to a person skilled in the art.

In the present invention, the concepts of "first" and "second" used in any cases should not be construed as conveying the meaning of order or technique, and they serve only to distinguish the objects to which they refer from other objects.

In the present invention, the first affinity label and the second affinity label can be a component in a biological binding reaction commonly used in biology, such as an antigen or antibody, a strand of a short double-stranded DNA fragment, a biotin or streptavidin, and the like. When an antigen is selected as the first affinity label, an antibody that binds to the antigen is selected as the second affinity label, and vice versa. When a strand of a short double-stranded DNA fragment is selected as the first affinity label, the other strand complementary to the strand is selected as the second affinity label, and vice versa; and when a biotin is selected as the first affinity label, a streptavidin that binds to the biotin is selected as the second affinity label, and vice versa. In an embodiment of the present invention, the first affinity label is a biotin lab el, and the second affinity label is a streptavidin label, both label strongly binding to each other.

Figure 1:
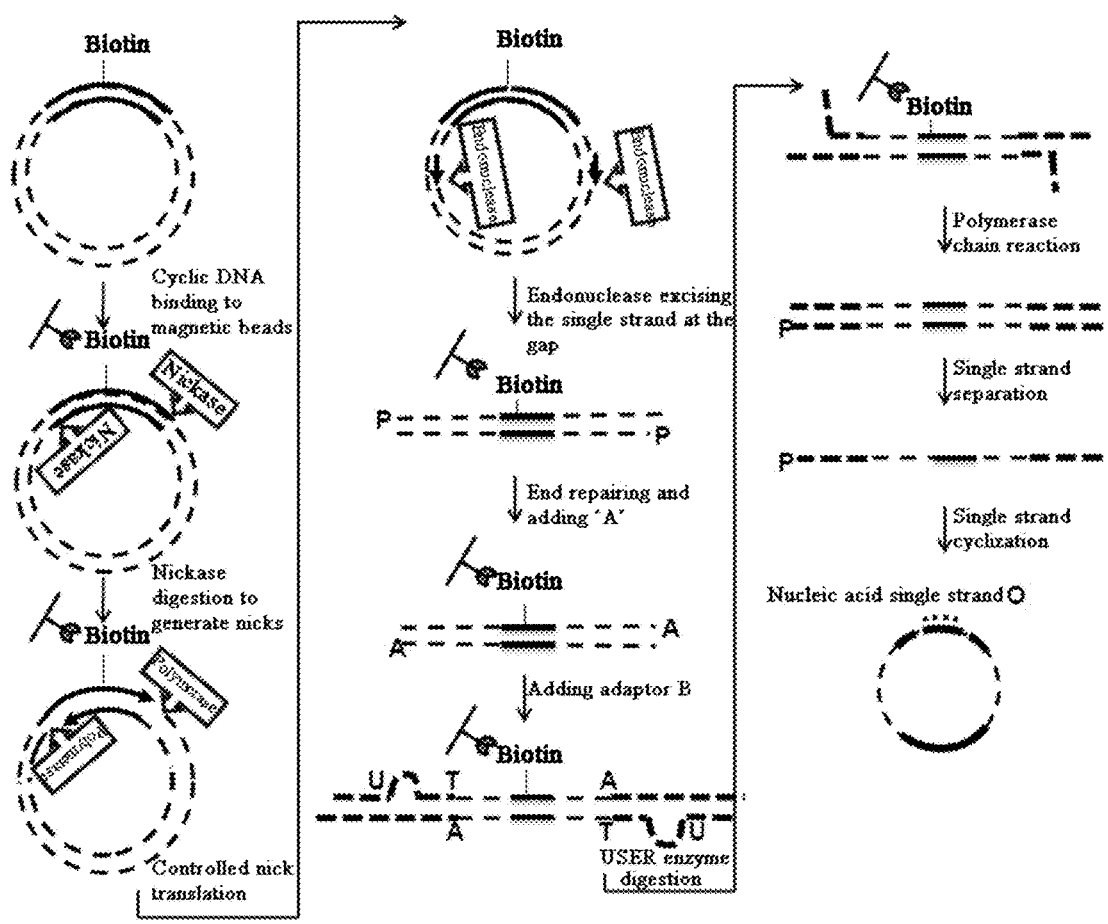
FIG. 1 is the flow-process diagram showing the process from binding to magnetic beads to cyclizing the single strands in the method for constructing a library of single-stranded cyclic nucleic acid fragments having double adaptors according to an embodiment of the present invention.

Reference is made to FIG. 1, in which a method for constructing a library of single-stranded cyclic nucleic acid fragments having double adaptors according to an embodiment of the present invention is shown. The method comprises the following steps: disrupting a genomic DNA to form nucleic acid fragments for constructing the library; subjecting the fragments to dephosphorylation and end repairing reactions; ligating a 5' adaptor A sequence to the fragments; subjecting the fragments to USER enzyme digestion and phosphorylation treatment; ligating a 3' L-type adaptor A sequence to the fragments; subjecting the fragments to PCR amplification to obtain products having the 5' adaptor A sequence and the 3' L-type adaptor A sequence at both ends, wherein the sequence of the primers used in the PCR comprises a U base site and a nickase recognition sequence, and one of the primers harbors a biotin label; digesting the U base site with a USER enzyme to generate sticky ends, and cyclizing the products following USER enzyme digestion to generate cyclic nucleic acid molecules; binding the cyclic nucleic acid molecules to streptavidin-labeled magnetic beads; digesting the cyclic nucleic acid molecules at the nickase recognition sequence with a nickase to generate nicks; initiating controlled nick translation (CNT) reaction from the nick; cleaving the nucleic acid strands at the nick with an endonuclease (or alternatively, first degrading the nucleic acid strands with a double strand exonuclease until the gaps at both ends meet, and then degrading a single strand with a single strand exonuclease) to obtain linear nucleic acid molecules; subjecting the linear nucleic acid molecules to end repairing and to a reaction of adding A base to the 3' end; ligating a bubble-type adaptor sequence; digesting the U base site on the bubble-type adaptor sequence with a USER enzyme to form an L-type adaptor; conducting PCR amplification to obtain products having different sequences on both ends; subjecting the products to denaturation treatment to obtain single-stranded nucleic acid molecules, and cyclizing one of the single-stranded nucleic acid molecules with a mediating sequence complementary to both ends of the single-stranded nucleic acid molecule to obtain the library of single-stranded cyclic nucleic acid fragments having double adaptors.

Figure 2:
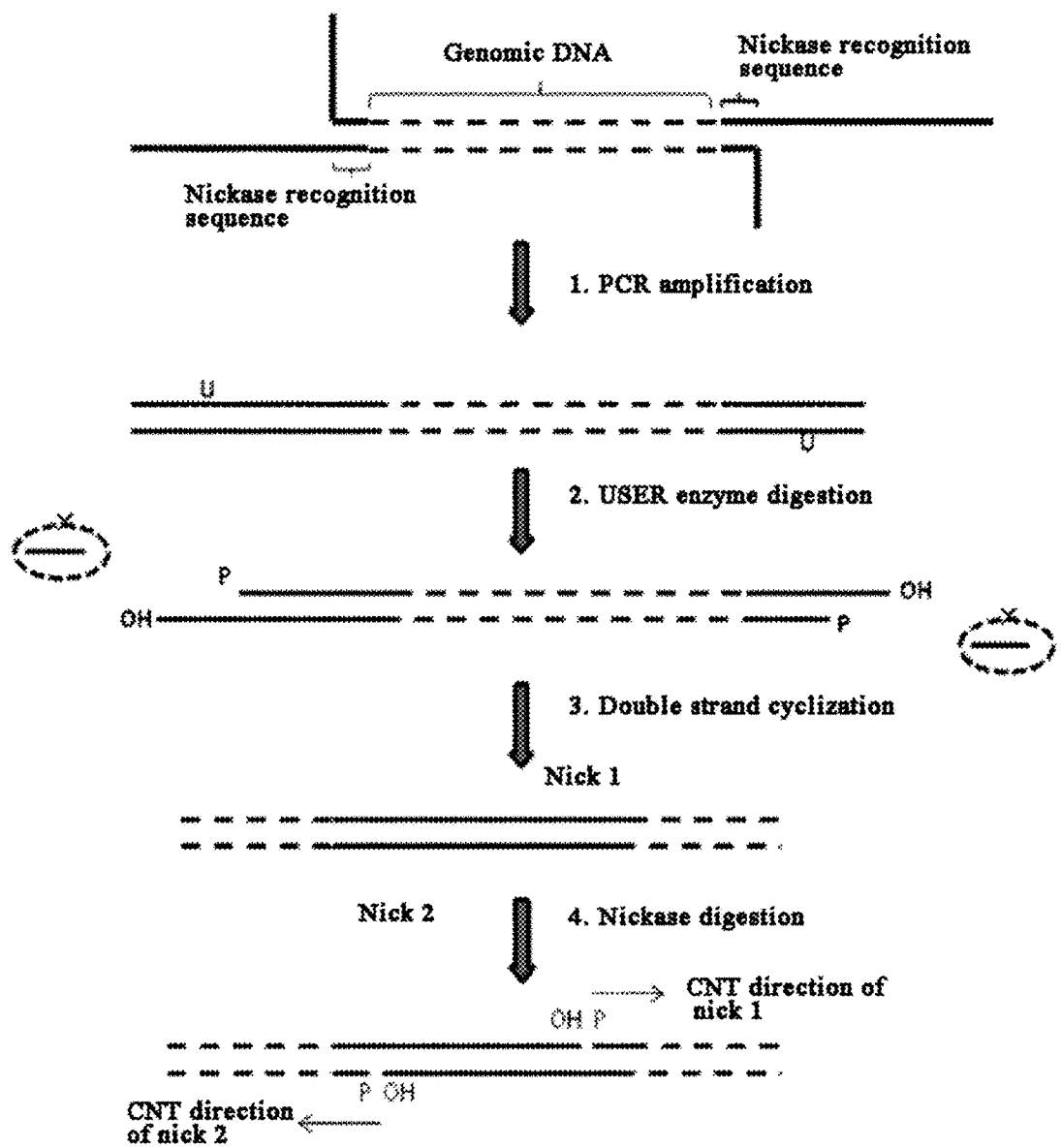
FIG. 2 is a diagram showing the basic principle underlying the generation of CNT nicks according to an embodiment of the present invention.

In the method according to the present invention for constructing a library of single-stranded cyclic nucleic acid fragments having double adaptors, as shown in FIG. 1, a U base site and a nickase recognition sequence are introduced into the primers for the first PCR, and nicks are generated by employing the principle as shown in FIG. 2, as the initiation point for the controlled gap translation reaction. In a prior art process, a III class endonuclease recognition sequence is introduced into the adaptor sequence, and following adaptor sequence ligation and cyclization, the double strands are digested with a III class endonuclease to generate linear double-stranded DNA; while in a process of the present invention, a U base site and a nickase recognition sequence are introduced into the primer sequences used in the first PCR, and following PCR amplification, the U base site is digested with a USER enzyme to generate sticky ends followed by performing double strand cyclization, then each single strand of the cyclized DNA is digested with a nickase (such as Nb.BsrDI, Nb.BsmI, Nt.BbvCI, Nb.Bbv.Nb.BtsI or Nt.BstNBI, etc.) to generate a nick on each single strand, so as to provide an effective initiation site for CNT.

Figure 3:
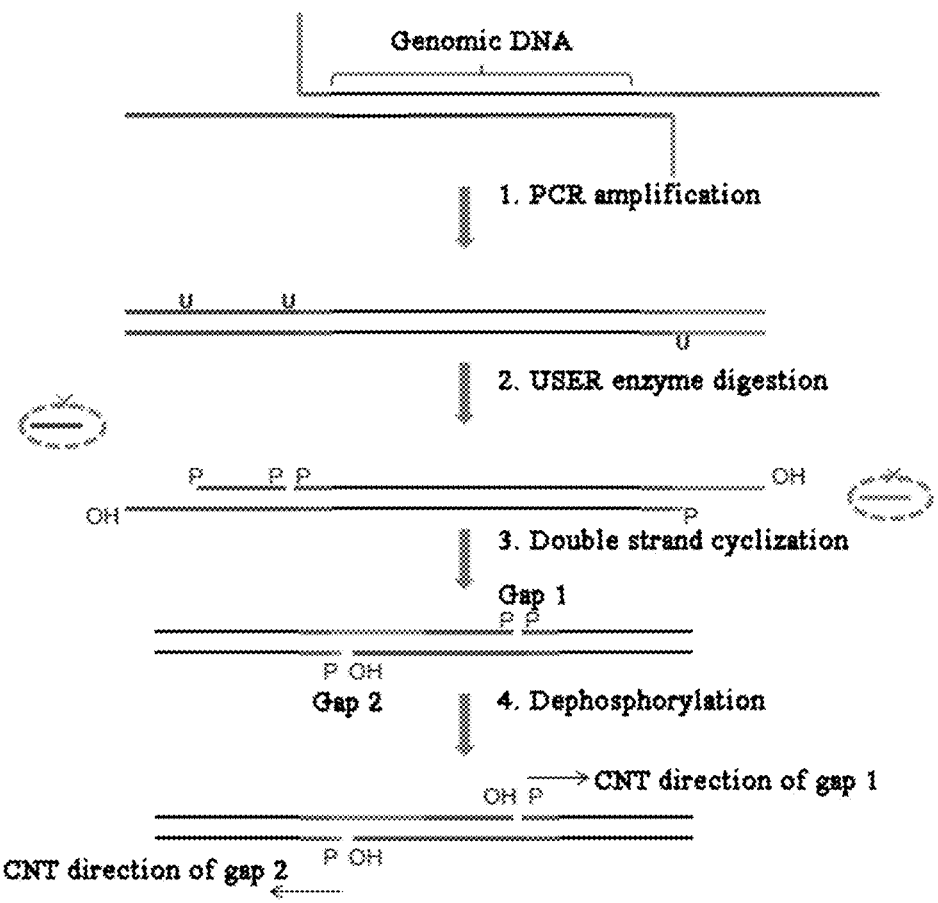
FIG. 3 is a diagram showing the basic principle underlying the generation of CNT gaps according to an embodiment of the present invention.

In an alternative embodiment of the present invention, a U base site is introduced into the primers for the first PCR, and is digested with a USER enzyme to generate a gap as an initiation point for the controlled gap translation reaction. 3The basic principle underlying the generation of the gap is as shown in FIG. 3: (1) after ligating the 5' adaptor A sequence and the 3' L-type adaptor A sequence, the adaptor A ligation products are amplified using primers respectively having two Us and one U; (2) the U bases are digested with a USER enzyme, forming phosphorylated 3' ends and 5' ends at the nicks; (3) performing double strand cyclization by means of the sticky ends generated in the enzyme digestion, wherein after cyclization, the gap on one strand (gap 1, formed by USER enzyme digestion) involves a phosphorylated 3' end and a phosphorylated 5' end, and the gap on the other strand (gap 2, formed due to lack of a matching base at the site after cyclization) involves a dephosphorylated 3' end and a phosphorylated 5' end; and (4) performing dephosphorylation treatment to dephosphorylate the 3' end of gap 1, so as to provide an effective initiation site for CNT.

In the present invention, the reaction initiated from the nick and/or gap is referred to as "controlled gap translation reaction", because the length of the target fragments generated by the reaction can be controlled in a certain range by controlling the usage amount of dNTPs, the usage amount of the nucleic acid molecules as template, the enzyme reaction temperature and time, among other factors. Nucleic acid fragments having a length in a certain range are suitable for a particular sequencing platform. In general, the length of the target fragments in the present invention is preferably controlled in the range of 50-250 bp. Such a length is several times longer than the length of the target fragments obtained by a conventional library construction protocol for a CG sequencing platform.Moreover, the CNT technique of the present application allows for controlling the library insert fragments in a very narrow range without performing gel recovery, which effectively enhances the operability of the gap translation technique.

Figure 4:
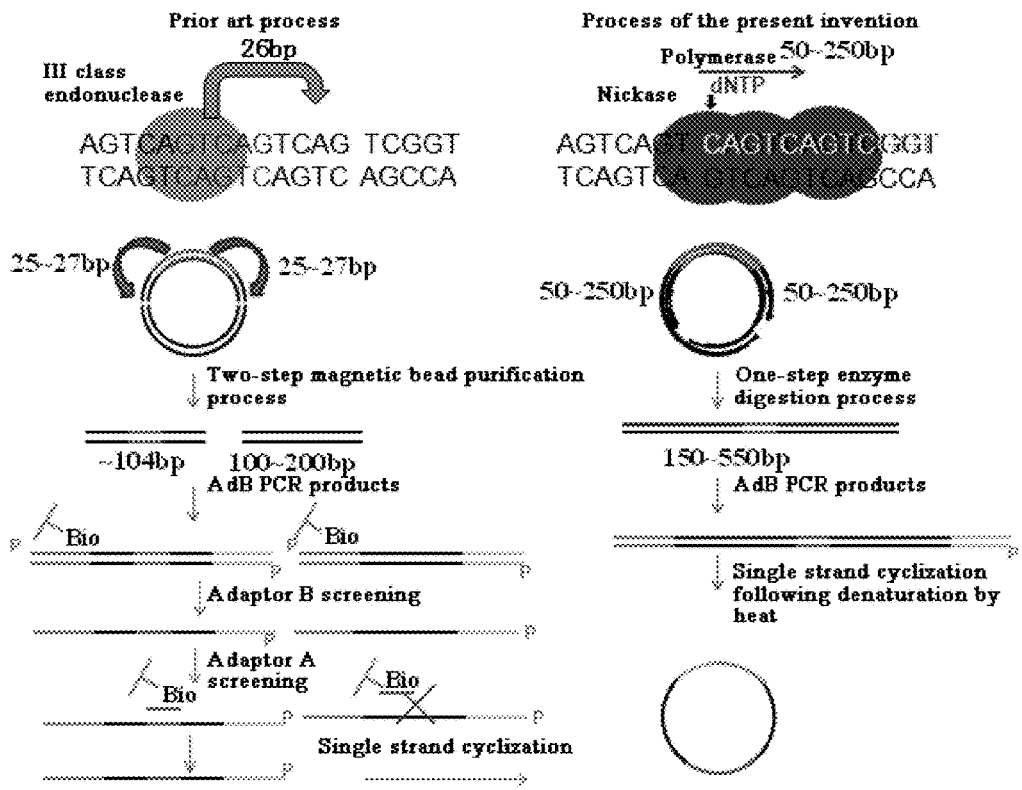
FIG. 4 is a diagram comparing the principle of formation of insert fragments and separation and cyclization of single strands according to a prior art process and the process of the present invention.

Reference is now made to FIG. 4, in which a prior art process and a process of the present invention are compared. The prior art process takes advantage of the cleaving property of a III class endonuclease, which digests the genomic DNA 25-27 bp from both sides of the adaptor A, forming a target DNA fragment of about 104 bp. Subsequently, the DNA fragments of more than 200 bp not having the adaptor A are removed by means of a two-step magnetic bead purification process. Following this sequence selection with magnetic beads, the digestion products obtained are still mingled with some non-target DNA fragments having main bands of 100-200 bp. Following ligation of the adaptor B, the DNA fragments ligated with the adaptor B are amplified with primers having a biotin-labeled base on one of the primers, wherein the single strands amplified with the primer having a biotin-labeled base thereon are non-target single-stranded nucleic acids. Subsequently, DNA fragments ligated with the adaptor B are enriched using streptavidin magnetic beads, and further, DNA fragments ligated with the adaptor A are enriched by capturing via specific sequence hybridization. Finally, the double-stranded DNA is unwound by means of alkali denaturation to elute the target single-stranded nucleic acids from the streptavidin magnetic beads, and then the target single-stranded nucleic acids are cyclized using a mediating sequence. The whole procedure of the prior art process not only involves tedious steps and lengthy operations, but also consumes expensive reagents (especially, Ampure magnetic beads or streptavidin magnetic beads are needed in the reaction of each step). With respect to the method of the present invention, on the one hand, the biotin label harbored on one of the primers for the first PCR allows the cyclic nucleic acid molecules obtained following cyclization to bind to streptavidin magnetic beads, with the target nucleic acid molecules remaining bound to the magnetic beads in subsequent reactions, such that no purification to be performed by adding new magnetic beads is required in each reaction step, and what is only needed for the following reaction step to proceed is to wash off the reaction solution with a washing reagent. This not only reduces the usage of magnetic beads, but also saves the time in experimental operations. On the other hand, a nick is made using a nickase on the two strands of adaptor A respectively. Then, by taking advantage of the nick translation function of a polymerase in the presence of dNTPs, the nicks are moved from the adaptor A region to either side of the adaptor A. The length through which the nicks are moved can be flexibly controlled by controlling the molar ratio of the dNTPs to the template DNA, the reaction temperature and the reaction time, among other conditions, and the size of the main band of the fragments through which the nicks are moved can be controlled in the range of 50-250 bp. Subsequently, the non-target DNA fragments not having adaptor A are digested by a one-step exonuclease digestion reaction, the remaining fragments being the target DNA fragments having adaptor A, which are subjected to ligation with adaptor B and PCR amplification using primers not having a biotin label. The resulting double-stranded DNAs are unwound simply by high temperature denaturation, and the resulting target single strands are cyclized by means of a mediating sequence, thus separating and cyclizing the target single-stranded DNAs.It can be seen that the single strand cyclization process of the present invention only entails denaturation by heat and hybridization with a mediating sequence for the successful separation and cyclization of the target single-stranded nucleic acids. Hence, the process of the present invention not only involves simple steps and easy operations, but also eliminates the need to consume large amounts of expensive reagents, leading to decreased cost in library construction.

Figure 5:
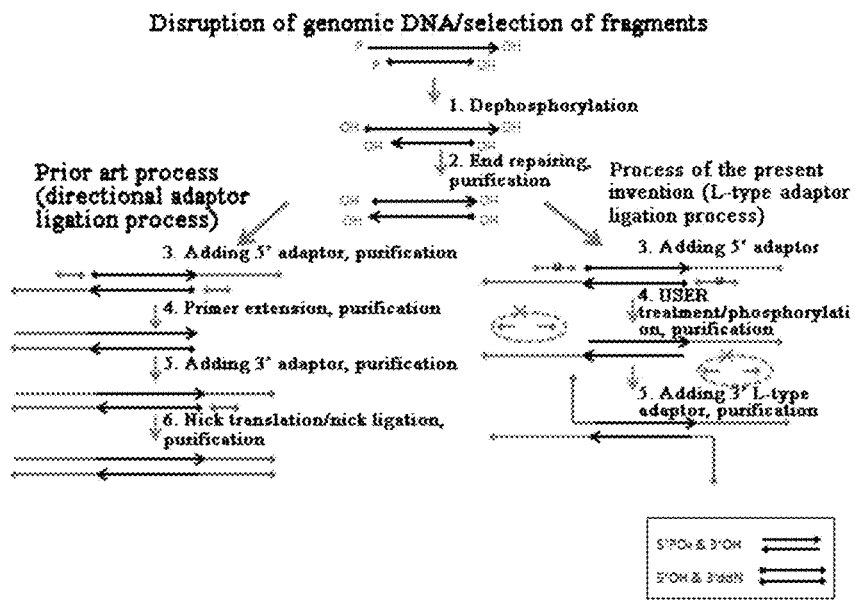
FIG. 5 is a diagram comparing a directional adaptor ligation process of the prior art and the L-type adaptor ligation process of the present invention.

In a preferred embodiment of the present invention, ligation is performed using an L-type adaptor instead of a conventional adaptor. Reference is now made to FIG. 5, in which a prior art adaptor ligation process and the adaptor ligation process of the present invention are compared. The prior art process employs a directional adaptor ligation process, whereby directional ligation of the adaptors is ensured and at the same time the problem of inter-ligation of DNA fragments is minimized. The prior art process involves separately designing and stepwise ligating the 5' adaptor and the 3' adaptor. The addition of an adaptor on either end entails synergy of an adaptor sequence, a blocking sequence and a primer sequence. The whole procedure entails 6 enzymatic reaction steps, i.e., dephosphorylation, end repairing, adding 5' adaptor, primer extension, adding 3' adaptor, nick translation and ligation, as well as 5 purification operations, in order to directionally add the sequence of adaptor A to both ends of the target DNA. Such a prior art process suffers from tedious steps, high cost and long period in library construction (the cost of sequences, the cost of enzymatic reaction reagents, and the cost of purification) and high consumption of samples, which does not comply with the requirement of high efficiency and convenience for library construction. On the contrary, the L-type adaptor ligation process of the present invention can increase library construction efficiency and decrease library construction cost while ensuring directional ligation of the adaptors. Although the L-type adaptor ligation process also employs stepwise ligation, the steps involved are simple in comparison to the prior art process. First, a 5' adaptor having a blocking sequence is added. The blocking sequence is 12 bp long and completely complementary to the 5' adaptor, forming a partially complementary double-stranded structure to facilitate ligation of DNA fragments with the 5' adaptor. The blocking sequence has a dideoxy modification at the 3' end and a dephosphorylized base at the 5' end. This not only ensures that the 5' end adaptor is directionally ligated to the 3' end of DNA fragments, but also that the blocking sequence would not ligate to the 5' end of DNA fragments. The blocking sequence has a U base in the middle, such that upon treatment with a USER enzyme, the blocking sequence is "degraded" into two single-stranded DNA fragments of smaller than 8 bp and thus is unwound and detached from the 5' adaptor. Then, an "L" type single-stranded 3' adaptor is added via a process of hybridization followed by ligation. Prior to addition of the L-type adaptor, the 5' end of the DNA fragments needs to be phosphorylated for deblocking. Experiments demonstrated that USER enzyme treatment can be performed concurrently with phosphorylation reaction. Following reaction, purification is conducted with magnetic beads, and the magnetic beads having been washed can be directly resuspended in a ligation reaction buffer for the next step. The L-type adaptor is so ingeniously designed that the last 8 bases at the 3' end thereof are complementary to the last 8 bases at the 5' end of the 5' adaptor, such that the L-type adaptor can directly hybridize to the 5' adaptor. Then, by using a ligase to block the nick, the L-type 3' adaptor is ligated to the 5' end of the DNA fragments. As some of the bases of the L-type adaptor are complementary to some of the bases at the 5' end of the 5' adaptor, while the other bases are not complementary to each other, the adaptor appears an L form, hence called L-type adaptor. After the reaction ends, the ligation products having added with the adaptors can be purified and recovered by further adding a suitable amount of a magnetic bead binding buffer into the magnetic beads. The sequence of adaptor A can be directionally added to both ends of the target DNA relatively fast only through five enzymatic reaction steps, i.e., dephosphorylation, end repairing, adding 5' adaptor, one-step reaction of USER digestion and phosphorylation, adding 5' L type adaptor, as well as three purification operations in the whole procedure. Thus, the steps are simple, the cost of library construction is lowered, and the period of library construction shortened.

The unique innovations of the present invention are mainly as follows: the enzymatic reactions are performed on streptavidin magnetic beads and can be performed following binding of nucleic acids to the streptavidin magnetic beads, without the need to elute the nucleic acids; and double-stranded nucleic acids having a particular length are generated using controlled gap translation reaction.

The cyclic acid molecules bind to the streptavidin magnetic beads via the biotin label. In each subsequent step of enzymatic reaction, the nucleic acid molecules remain bound to the magnetic beads. Throughout these steps, the enzymes and ions in the reactions can simply be removed by washing operations, in which the double-stranded nucleic acids harboring the biotin label would not be eluted. Only after the second PCR will the double-stranded nucleic acids be denatured into two single strands, and then the single strands not having the biotin label are collected.

In conventional experimental operations of Complete Genomics Corporation, enzymatic reactions are performed in a solution. After each step of enzymatic reaction, the target fragments need to be bound by newly added magnetic beads, the enzymes and buffers and the like in the reaction need to be washed, and finally the target fragments need to be eluted for reaction in the following step. On the contrary, the enzymatic reactions in the present invention are performed on streptavidin magnetic beads, and it suffices to add the magnetic beads once. After the double-stranded nucleic acid molecules bind to the magnetic beads, no multiple and repeated operations of eluting and of adding new magnetic beads for rebinding are needed. The desired target fragments can be collected by a simple washing operation, omitting the fragment purification operation in a number of steps. This not only saves the time in experimental operations, but also decreases the usage amount of magnetic beads, thus reducing the cost. Moreover, as repeated operations of binding and eluting with respect to the samples and the magnetic beads are avoided, the loss of experimental samples is reduced and the yield of the final target fragments is increased. In an embodiment of the present invention, magnetic beads are used as the solid-phase carrier. However, the solid-phase carrier is not limited to magnetic beads, but can also be chips or other solid-phase carriers. The purpose of the present invention is be achieved so long as streptavidin is bound to a solid-phase carrier.

In the conventional library construction process of Complete Genomics Corporation, a III class enzyme digestion site is present on the cyclic DNA. After the III class enzyme recognizes the digestion site, it will digest the cyclic DNA 26 bp from the digestion site, turning the cyclic DNA into two linear DNA fragments. Then the target fragments can be collected by means of binding of the biotin label on the DNA to streptavidin magnetic beads. In such a process, target fragments obtained after digestion are only 26 bp, restricting the fragment size of the library. Moreover, the enzymatic reactions take a long time of up to 16 hours. On the contrary, the present invention employs the gap generated during cyclization, or replaces a III class enzyme recognition site with a nickase recognition site. After the cyclic DNA binds to streptavidin magnetic beads, the two strands are digested, forming a gap or nick respectively thereon. Then the translation of the gap or nick is achieved by virtue of the 5'-3' polymerase activity and 3'-5' exonuclease activity of a polymerase, such that both strands of the target fragments undergo polymerization-extension starting from the gap or nick in the 5'-3' direction, thus increasing the length of library insert fragments. The length of the fragments can be controlled by controlling reaction conditions. The reaction conditions to be controlled include the usage amount of dNTPs, the usage amount of the polymerase, temperature, time, among others. When the dNTPs are depleted, the DNA polymerase will further function as an exonuclease and continue to excise in the 3'-5' direction of the strand to generate sufficiently large gaps. At last, the other single strand is excised at the gaps by a single strand endonuclease, forming double-stranded nucleic acids with both ends. The target fragments to be recovered harbor biotin labels, which have already bound to streptavidin magnetic beads, on which enzymatic reactions can be performed. Therefore, the target fragments can be obtained by simple washing operations to remove the enzymes, buffers, etc., in the reactions and then used in subsequent reactions. With this process, the enzymatic reaction takes about 2.5 hours. In comparison with a conventional process, this not only shortens the time, but also increases the length of the final library insert fragments and achieves control over the length of the fragments.

The present invention is illustrated in detail with reference to the following example.

1. Disruption of genomic DNA: Genomic DNA can be disrupted in a number of methods, and no matter they are a physical ultrasonic method or an enzymatic reaction method, well-established protocols are commercially available. In this example, the physical ultrasonic method was employed for disruption.

A 96-well PCR plate was added with a polytetrafluoroethylene line. 1 µg of genomic DNA was added, then TE buffer solution or enzyme-free pure water was added to make up to 100 µt. The plate was sealed with a membrane and then placed in an E220 ultrasonic disruptor to conduct ultrasonic disruption. The conditions for disruption were shown in Table 1.

TABLE 1

| Parameter | Value |
| --- | --- |
| Filling factor | 21% |
| Pressure (PIP) | 500 |
| Pulse factor | 500 |
| Disruption time | 20 s, twice |

2. Selection of fragments following disruption: A magnetic bead purification method or gel recovery method can be employed. In this example, the magnetic bead purification method was used.

The disrupted DNA was added with 45 µL of Ampure XP magnetic beads, and the mixture was mixed well and stood for 7-15 min. The resulting mixture was placed on a magnetic rack, and supernatant was collected. The supernatant was added with 18 µL of Ampure XP magnetic beads, and the mixture was mixed well and stood for 7-15 min. The resulting mixture was placed on a magnetic rack, and supernatant was aspirated off. The magnetic beads were washed twice with 75% ethanol and air dried. Then 30 µL of TE solution was added, and the mixture was mixed well and stood for 7-15 min to allow the recovered products to dissolve.

3. Dephosphorylation reaction of the fragments: The recovered products from the previous step were used, and a system was formulated according to Table 2.

TABLE 2

| Reaction component | Volume (µL) |
| --- | --- |
| 10x NEB buffer 2 | 3.6 |
| Shrimp alkaline phosphatase (1 U/µL) | 3.6 |
| Total | 7.2 |

7.2 µL of the reaction solution was added to the recovered products from the previous step. The mixture was mixed well and incubated at 37° C. for 45 min and at 65° C. for 10 min. Then the temperature was ramped down to 4° C. at a rate of 0.1° C. per second.

4. End repairing of the fragments. A system was formulated according to Table 3.

TABLE 3

| Reaction component | Volume (µL) |
| --- | --- |
| Enzyme-free water | 7.32 |
| 10x NEB buffer 2 | 1.08 |
| 0.1M adenosine triphosphate | 0.48 |
| dNTPs (25 mM, Enzymatic) | 0.48 |
| Bovine serum albumin (10 mg/ml) | 0.24 |
| T4 deoxyribonucleic acid polymerase (3 U/µL) | 1.2 |
| Total | 10.8 |

The system was mixed well and the products from the previous step were added. The mixture was mixed well and incubated at 12° C. for 20 min. The reaction was purified with 48 µL of Ampure XP magnetic beads, and the recovered products were dissolved using 40 µL of TE buffer solution.

5. Ligation of 5' adaptor A sequence: The 5' adaptor A sequence used in this example was as follows (in this example, the sequences are shown in the direction of from 5' end to 3' end from left to right, "//" represents modification group, "phos" represents phosphorylation, "dd" represents dideoxy, "bio" represents biotin, and the characters in bold represent a tag sequence).

```
5' adaptor A sequence:
                                      (SEQ ID NO: 1)
/5phos/AAGCTGAGGGTACTGTGTCATAAATAGCACGAGACGTTC
TCGACT;

5' blocking sequence:
                                      (SEQ ID NO: 2)
TACCCUCAGCT/3ddT/.
```

A mixed solution of 5' adaptor A (10 µM) was formulated according to Table 4.

TABLE 4

| Reaction component | Volume (µL) |
| --- | --- |
| 5' adaptor A sequence (100 µM) | 12 |
| 5' blocking sequence (100 µM) | 10 |
| TE buffer | 78 |
| Total | 100 |

4.5 µL of the mixed solution of 5' adaptor A formulated (10 µM) was added into the products of the previous step, and the mixture was sufficiently mixed.

A ligation reaction system was formulated according to Table 5.

TABLE 5

| Reaction component | Volume (μL) |
| --- | --- |
| Enzyme-free pure water | 13.1 |
| 2x ligation buffer 1 | 60 |
| T4 DNA ligase (fast) (600 U/μL) | 2.4 |
| Total | 75.5 |

The 2× ligation buffer 1 used in this example was formulated according to Table 6.

TABLE 6

| Reaction component | Volume (μL) |
| --- | --- |
| 1M tromethamine | 37.5 |
| 1M citric acid | 9.6 |
| 1M magnesium chloride | 35 |
| 1M trisodium citrate | 20 |
| 100% glycerol | 50 |
| 10% Tween-80 | 1 |
| 30% polyethylene glycol 8000 | 333 |
| 0.1M adenosine triphosphate | 10 |
| 0.5M trichloroethyl phosphate (pH 7.0) | 2 |
| Enzyme-free pure water | 1.9 |
| Total | 500 |

A mixed solution of the ligation reaction system with the adaptor and the products was mixed well, and the mixture was incubated at 25° C. for 30 min and at 65° C. for 10 min, followed by decreasing the temperature to 4° C.

6. One-step reaction of USER enzyme digestion and phosphorylation: Into the reaction solution from the previous step were added 1.2 μL of USER enzyme (1 U/μL) and 1.2 μL of T4 polynueleotide kinase (10 U/μL). The mixture was mixed well and incubated at 37° C. for 20 min. The reaction was purified with 108 μL of Ampure XP magnetic beads (Agencourt). The beads were rinsed with 70% ethanol twice, and with the rinsing liquid having been blot up, were air dried at room temperature for 2 min. Then the beads were resuspended in 48 ||L of a 3' L-type adaptor reaction system.

7. Ligation of 3' L-type adaptor A sequence: The 3' L-type adaptor A sequence used in this example was as shown below: ACGTTCTCGACUCCTCAGCTT (SEQ ID NO: 3).

The 3' L-type adaptor reaction system was formulated according to Table 7:

TABLE 7

| Reaction component | Volume (μL) |
| --- | --- |
| Enzyme-free pure water | 28.98 |
| 3x ligation buffer 2 | 16.02 |
| L-type adaptor sequence (100 μM) | 1.8 |
| T4 DNA ligase (fast) (600 U/μL) | 1.2 |
| Total | 48 |

The 3× ligation buffer 2 used in this example was formulated according to Table 8.

TABLE 8

| Reaction component | Volume (μL) |
| --- | --- |
| polyethylene glycol-8000 (50%) | 60 |
| Tris-Cl, pH 7.8 (2M) | 7.5 |

TABLE 8-continued

| Reaction component | Volume (μL) |
| --- | --- |
| Adenosine triphosphate (100 mM) | 3 |
| Bovine serum albumin (10 mg/mL) | 1.5 |
| Magnesium chloride (1M) | 3 |
| Dichlorodiphenyltrichloroethane (DDT) (1M) | 0.15 |
| Enzyme-free pure water | 24.9 |

The Ampure XP magnetic beads resuspended in 48 μL of the 3' L-type adaptor reaction system was incubated in an incubator at a rotation speed of 300 rpm at 25° C. for 30 min. After reaction was complete, 43.2 μL of Ampure XP magnetic bead binding buffer was added to conduct incubation at room temperature for 10 min. The supernatant was removed and the beads were washed with 70% ethanol twice, followed by air dried at room temperature for 5-10 min. The recovered products were dissolved with 30 μL of TE buffer solution.

8. Polymerase chain reaction:

The sequence of primer 1 was as follows:

(SEQ ID NO: 4)
AGTCGAGAACGUCTCG/iBiodT/GCT;

The sequence of primer 2 was as follows:

(SEQ ID NO: 5)
ACGTTCTCGACUCCTCAGCTT.

A PCR system was formulated according to Table 9.

TABLE 9

| Reaction component | Volume (μL) |
| --- | --- |
| Enzyme-free pure water | 186.5 |
| 2x PfuTurbo Cx buffer | 275 |
| PfuTurbo Cx heat-activated nucleic acid polymerase (2.5 U/μL) | 11 |
| 20 μM primer 1 | 13.75 |
| 20 μM primer 2 | 13.75 |
| Total volume | 500 |

Into the above system was added 50 μL (180 ng) of the recovered products from the previous step. The mixture was mixed well and reaction was allowed under the conditions set out in Table 10.

TABLE 10

| Temperature | Time | Cycle |
| --- | --- | --- |
| 95° C. | 3 min | 1 |
| 95° C. | 30 s | 7 |
| 56° C. | 30 s | |
| 72° C. | 4 min | |
| 68° C. | 10 min | 1 |
| Ramping the temperature down to 4° C. at a rate of 0.1° C./s | | |
| 4° C. | Holding the temperature | — |

After reaction was complete, purification was conducted using 550 μL of Ampure XP magnetic beads, and the recovered products were dissolved with 80 μL of TE buffer. 1 μL of the recovered products was assayed with a Qubit dsDNA HS assay kit (Invitrogen Corp.) to quantitate the concentration of the products. 2 μL of the products was used for reaction at the next step.

9. Removal of uracil: A reaction solution as shown in Table 11 below was formulated.

TABLE 11

| Reaction component | Volume (μL) |
| --- | --- |
| Enzyme-free pure water | 25.8 |
| 10x Taq buffer | 11 |
| USER enzyme (1 U/μL) | 13.2 |
| Total volume | 50 |

The above reaction solution was added into 60 μL (2 μg) of the reaction products from the previous step, and the mixture was mixed well and incubated at 37° C. for 1 h.

10. Double strand cyclization: Reaction system 1 as shown in Table 12 below was formulated.

TABLE 12

| Reaction component | Volume (μL) |
| --- | --- |
| Enzyme-free pure water | 1520 |
| 10x TA buffer | 180 |
| Total volume | 1700 |

The reaction products from the previous step were added into reaction system 1. The mixture was mixed well and evenly dispensed into 4 tubes. The tubes were placed in a water bath at 50° C. for reaction for 15 min. After the reaction was complete, the tubes were placed in a water bath at ambient temperature for reaction for 15 min.

Reaction system 2 as shown in Table 13 below was formulated.

TABLE 13

| Reaction component | Volume (μL) |
| --- | --- |
| Enzyme-free pure water | 98 |
| 20 × Circ buffer | 100 |
| T4 DNA ligase (fast) (600 U/μL) | 2 |
| Total volume | 200 |

The 20×Circ buffer used in the example was formulated according to Table 14.

TABLE 14

| Reaction component | Concentration |
| --- | --- |
| Tris-Cl, pH 7.5 | 66 mM |
| Potassium acetate | 132 mM |
| Magnesium acetate | 20 mM |
| Dichlorodiphenyltrichloroethane (DDT) | 1 mM |
| Adenosine triphosphate | 20 mM |

Into each of the 4 tubes of reaction system 1 was added 50 μL of reaction system 2, and the tubes were incubated at room temperature for 1 h.

330 μL of Ampure XP magnetic beads was added into the reaction products of each tube (500 μL). The mixture in each tube was mixed well and stood for 7-15 min. After placing the tubes on a magnetic rack, supernatant was collected. The supernatant was added with 170 μL of Ampure XP magnetic beads, and the mixture was mixed well and stood for 7-15 min. After placing the tubes on a magnetic rack, supernatant was aspirated off, and the magnetic beads were washed with 75% ethanol twice. After air drying the magnetic beads, 65 μL of TE buffer was added to each of the 4 tubes to dissolve the purified products.

11. Linear digestion: A reaction system as shown in Table 15 below was formulated.

TABLE 15

| Reaction component | Volume (μL) |
| --- | --- |
| Enzyme-free pure water | 0.7 |
| Plasmid-Safe 9X reaction buffer | 8.9 |
| Plasmid-Safe ATP-dependent DNase | 10.4 |
| Total volume | 20 |

The products from the previous step were added into the reaction system, and the mixture was mixed well and incubated at 37° C. for 1 h.

Purification was conducted using 80 μL of Ampure XP magnetic beads, and the recovered products were dissolved using 82 μL of TE buffer. 1 μL of the recovered products was assayed with a Qubit dsDNA HS assay kit (Invitrogen Corp.) to quantitate the concentration of the products. 700 ng of the products was used for reaction at the next step. The initiation site for CNT reaction on the double-strand cyclized DNA formed in this example is in the form of nick. That is, both are complete double-stranded cyclic DNAs, and the adaptor A sequence harbors a nickase recognition sequence.

12. Binding of cyclic DNA to magnetic beads: 500 ng of cyclic DNA was added to streptavidin magnetic beads (Life Technologies) and binding was allowed at room temperature for 1 h, such that the cyclic DNA bound to the streptavidin magnetic beads via the biotin label on the DNA. The resulting mixture was placed on a magnetic rack, and the supernatant was removed. The magnetic beads were washed with a high-salt wash solution once, washed with a low-salt wash solution once, and rinsed with 1×NEB buffer 2 once. The high-salt wash solution and the low-salt wash solution were respectively formulated according to Table 16 and Table 17.

TABLE 16

| Reaction component | Volume (μL) |
| --- | --- |
| Tris-Cl, pH 7.5 (1M, SIGMA) | 5000 |
| Sodium chloride (5M, SIGMA) | 10000 |
| Enzyme-free pure water | 35000 |
| Total | 50000 |

Before use, 10% Tween 20 was added to a final concentration of 0.05%.

TABLE 17

| Reaction component | Volume (μL) |
| --- | --- |
| Tris-Cl, pH 7.5 (1M, SIGMA) | 5000 |
| Sodium chloride (5M, SIGMA) | 3000 |
| Enzyme-free pure water | 42000 |
| Total | 50000 |

Before use, 10% Tween 20 was added to a final concentration of 0.05%.

13. Enzymatic digestion with nickase: A system was formulated according to Table 18 below.

TABLE 18

| Reaction component | Volume (μL) |
|---|---|
| Enzyme-free water | 66.3 |
| 10 × NEB buffer 2 | 8 |
| Nt.BvbCI | 1.7 |
| Total | 80 |

80 μL of the reaction solution was added to the magnetic beads from the previous step, and the mixture was mixed well to allow reaction at 37° C. for 60 min.

After reaction, the resulting mixture was placed on a magnetic rack, and the supernatant was removed. The magnetic beads were washed with the high-salt wash solution once, washed with the low-salt wash solution once, and rinsed with 1×NEB buffer 2 once.

14. Controlled gap translation reaction: A system was formulated according to Table 19 below.

TABLE 19

| Reaction component | Volume (μL) |
|---|---|
| Enzyme-free pure water | 48 |
| 10 × NEB buffer 2 | 6 |
| dNTPs (0.014 mM, Enzymatic) | 4.3 |
| DNA polymerase I (*E. coli*) (10 U/μL, NEB) | 1.8 |
| Total | 60 |

The usage amounts of dNTPs and DNA polymerase I are variable and can be adjusted according to the length of the target fragments desired.

60 μL of the reaction solution was added to the magnetic beads from the previous step, and the mixture was mixed well and allowed to react at 25° C. for 15 min. Then 1.2 μL of EDTA (0.5 M, AMBION) was added and the resulting mixture was allowed to react at 65° C. for 15 min.

After reaction, the resulting mixture was placed on a magnetic rack, and the supernatant was removed. The magnetic beads were washed with the high-salt wash solution once, washed with the low-salt wash solution once, and rinsed with 1×NEB buffer 2 once.

15. Digestion at the gap by an endonuclease: A system was formulated according to Table 20 below.

TABLE 20

| Reaction component | Volume (μL) |
|---|---|
| Enzyme-free pure water | 78 |
| 10 × NEB buffer 2 | 9 |
| T7 endonuclease I (10 U/μL, NEB) | 3 |
| Total | 90 |

90 μL of the reaction solution was added to the magnetic beads from the previous step, and the mixture was mixed well and allowed to react at 25° C. for 15 min. Then 2 μL of EDTA (0.5 M, AMBION) was added. After reaction, the resulting mixture was placed on a magnetic rack, and the supernatant was removed. The magnetic beads were washed with the high-salt wash solution once, washed with the low-salt wash solution twice, and then resuspended in 100 μL of the low-salt wash solution.

16. Filling of the sticky ends and addition of A at the 3' end: A system was formulated according to Table 21 below.

TABLE 21

| Reaction component | Volume (μL) |
|---|---|
| Enzyme-free pure water | 0.8 |
| 5 × Klex NTA mix | 26 |
| Klenow fragment (3'→5' exo-) (5 U/μL, NEB) | 3.2 |
| Total | 30 |

30 μL of the reaction solution was added to the resuspended magnetic beads from the previous step, and the mixture was mixed well and allowed to react at 37° C. for 60 min. Then 2 μL of EDTA (0.5 M, AMBION) was added. After reaction, the resulting mixture was placed on a magnetic rack, and the supernatant was removed. The magnetic beads were washed with the low-salt wash solution for three times, and then resuspended in 70 μL of the low-salt wash solution.

17. Ligation of adaptor B (bubble-type adaptor):

Adaptor B consisted of a top strand L and a bottom strand S which were complementary to each other, the strands having the following sequences:

```
Top strand L:
                                     (SEQ ID NO: 6)
/phos/AGTCGGAGGCCAAGCGTGCTTAGGACAT;

Bottom strand S:
                                     (SEQ ID NO: 7)
GTCCTAAGCACUGTAGTGTACGATCCGACTT.
```

A system was formulated according to Table 22 below.

TABLE 22

| Reaction component | Volume (μL) |
|---|---|
| Enzyme-free pure water | 21 |
| 3 × ligation buffer 2 | 56.8 |
| Adaptor B (10 μM) | 20 |
| T4 ligase (600 U/μL, Enzymatics) | 3.2 |
| Total | 100 |

100 μL of the reaction solution was added to the resuspended magnetic beads from the previous step, and the mixture was mixed well and allowed to react at room temperature for 30 min and then at 65° C. for 10 min.

18. USER enzyme digestion: 1 μL of USER enzyme (1 U/μL, NEB) was added, and the mixture was mixed well and allowed to react at 37° C. for 60 min. Then 4.5 μL of EDTA (0.5 M, AMBION) was added. After reaction, the resulting mixture was placed on a magnetic rack, and the supernatant was removed. The magnetic beads were washed with the low-salt wash solution for three times, and the single strands having no biotin label were separated by using 40 μL of 0.1 M sodium hydroxide. An acidic buffer was added to neutralize the products separated, the total volume of the products after neutralization being 60 μL. The other strands having biotin label remained bound to the magnetic beads.

19. Polymerase chain reaction:

The sequences of the primer F and primer R used in this example were as follows:

```
Primer F:
                              (SEQ ID NO: 8)
/bio/ATGTCCTAAGCACGCTTGGCC;

Primer R:
                              (SEQ ID NO: 9)
/phos/GTAGTGTACGATCCGACTT.
```

A system was formulated according to Table 23 below.

TABLE 23

| Reaction component | Volume (μL) |
|---|---|
| Single-stranded DNA from the previous step | 30 |
| Enzyme-free pure water | 160 |
| 2 × PfuCx buffer | 219.8 |
| PfuCx heat-activated nucleic acid polymerase (2.5 U/μL, Agilen) | 8.2 |
| Primer F (20 μM, Sangon) | 11 |
| Primer R (20 μM, Sangon) | 11 |
| Total volume | 440 |

After mixing well, reaction was allowed under the conditions shown in Table 24 below:

TABLE 24

| Temperature | Time |
|---|---|
| 95° C. | 3 min |
| 95° C. | 30 s |
| 56° C. | 30 s |
| 72° C. | 4 min |
| Repeating steps 2 to 4 for 7 times | |
| 68° C. | 10 min |

After reaction was complete, purification was performed using 400 μL of Ampure XP magnetic beads (Agencourt), and the recovered products were dissolved in 80 μL of TE buffer solution.

20. Single strand cyclization: Both ends of the products from the previous step could be ligated together by nucleic acid single strand O via corresponding complementary sequences. The sequence of nucleic acid single strand O was as follows:

```
                              (SEQ ID NO: 10)
ATCGTACACTACATGTCCTAAGCA.
```

100 ng of the PCR products from the previous step was added with 10 μL of nucleic acid single strand O (10 μM, Sangon). The mixture was mixed well and placed at 95° C. for 3 min, then rapidly placed on ice for cooling. A system was formulated according to Table 25 below.

TABLE 25

| Reaction component | Volume (μL) |
|---|---|
| Enzyme-free pure water | 36.4 |
| 10 × TA buffer (Epicentre Corp.) | 12 |

TABLE 25-continued

| Reaction component | Volume (μL) |
|---|---|
| 100 mM adenosine triphosphate (Epicentre Corp.) | 1.2 |
| T4 ligase (600 U/μL, Enzymatics) | 0.4 |
| Total | 50 |

50 μL of the reaction solution was added into a mixed solution of the PCR products and the single strand O, and the mixture was mixed well and allowed to react at 37° C. for 60 min.

21. Linear DNA digestion: A system was formulated according to Table 26 below.

TABLE 26

| Reaction component | Volume (μL) |
|---|---|
| Enzyme-free pure water | 2 |
| 10 × TA buffer (Epicentre Corp.) | 0.8 |
| Exonuclease 1 (20 U/μL, NEB Corp.) | 3.9 |
| Exonuclease 3 (100 U/μL, NEB Corp.) | 1.3 |
| Total | 8 |

8 μL of the reaction solution was added into the ligation reaction solution from the previous step, and the mixture was mixed well and allowed to react at 37° C. for 30 min; and 6 μL of EDTA (0.5 M) was added. Then, the products were purified and recovered using 170 μL of PEG32 magnetic beads, and redissolved in 55 μL of TE buffer.

Figure 6:
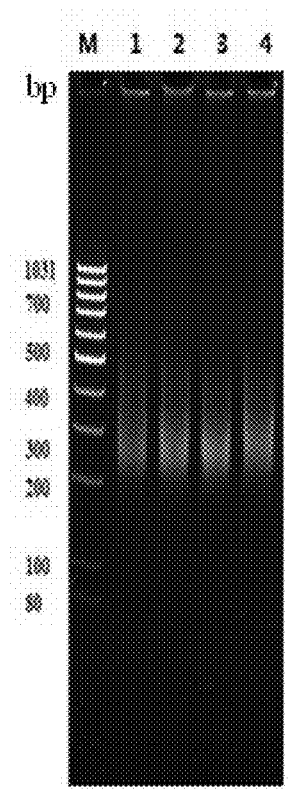
FIG. 6 shows the results of electrophoretic detection of the final products in the four parallel experiments according to an example of the present invention, wherein M represents DNA Marker; 1, 2, 3 and 4 respectively represent the electrophoresis results of the four parallel samples C22, D22, E22 and F22.
Figure 7:
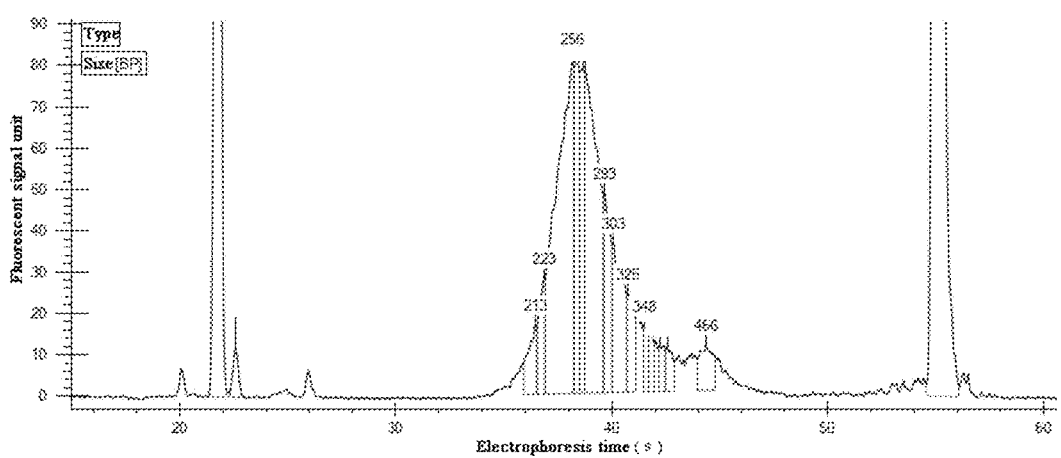
FIGS. 7-10 respectively show the results of the final products in the four parallel experiments C22, D22, E22 and F22 according to an example of the present invention, as detected using a LabChip GX instrument (fully automatic microfluidic electrophoresis device, Caliper Corp.).
Figure 8:
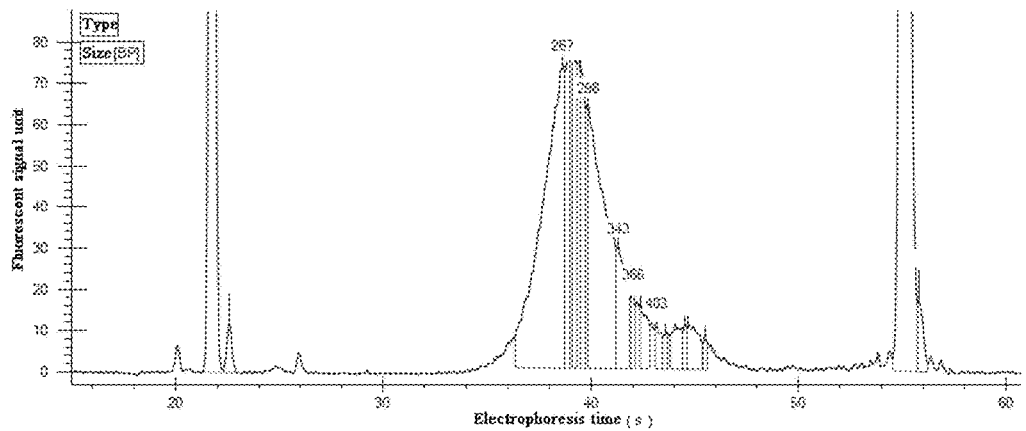
Figure 9:
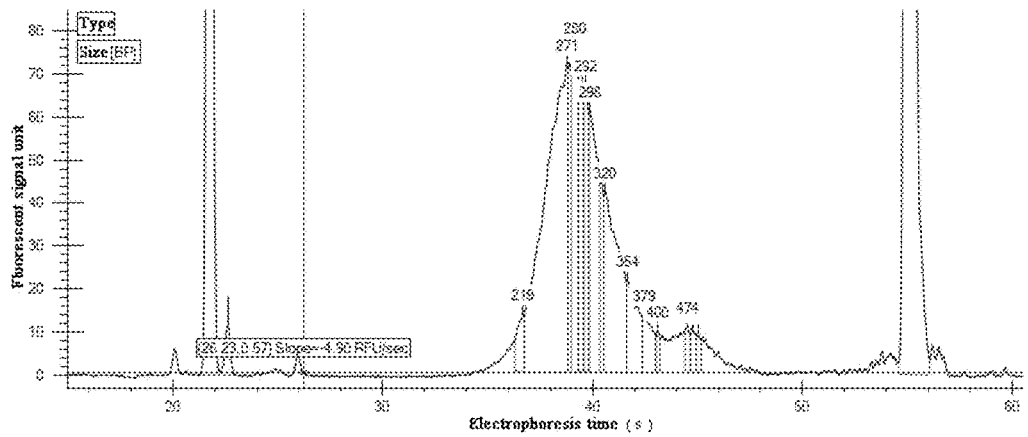
Figure 10:
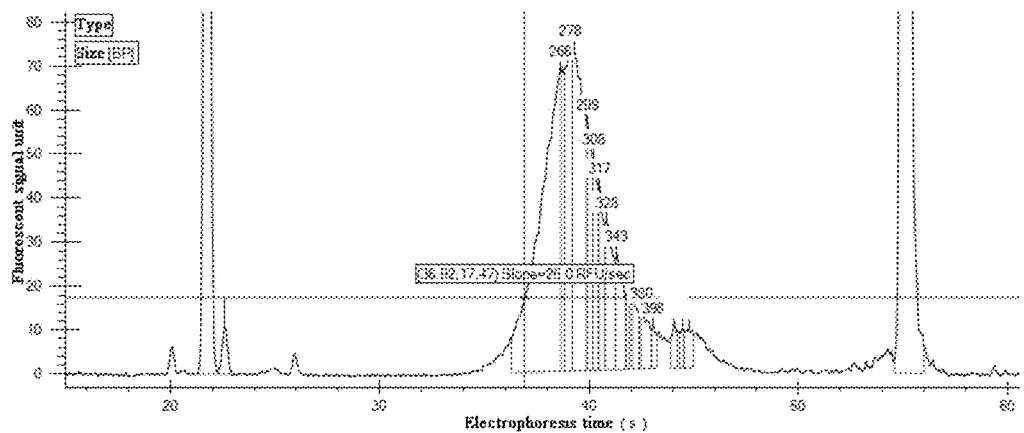

The concentration and total amount of the final products in the four parallel experiments in this example were as shown in Table 27 below. The results of electrophoresis were shown in FIG. 6.

TABLE 27

| Sample name | Concentration (ng/μL) | Total amount (ng) |
|---|---|---|
| C22 | 0.33 | 18.33 |
| D22 | 0.32 | 17.87 |
| E22 | 0.32 | 17.87 |
| F22 | 0.31 | 17.15 |

From the above table it can be seen that the concentration and total amount of the library were sufficient to meet the requirements of subsequent sequencing with respect to library size. Moreover, the results of electrophoresis (FIG. 6) and the results of detection using a LabChip GX instrument (fully automatic microfluidic electrophoresis device, Caliper Corp.) (FIGS. 7-10) indicated that the bands of the DNA library following polymerase chain reaction clustered together, the size of the fragments being from 200 bp to 300 bp, and the electrophoretic bands clustered together, the main peaks being prominent, which satisfied the requirements of subsequent sequencing with respect to the range of the fragments.

The disclosure set forth above is intended to describe the present invention in further detail by reference to particular embodiments, and is not to be construed as limiting the practical implementation of the present invention thereto. A number of simple deductions or substitutions could be made by a person of ordinary skill in the art to which the present invention pertains without departing from the concept of the present invention.

What is claimed is:

1. A method for constructing a library of single-stranded cyclic nucleic acid fragments having double adaptors, comprising the following steps carried out in the following order:
   (1) disrupting a nucleic acid into nucleic acid fragments for library construction and selecting disrupted fragments using magnetic bead purification or gel recovery;
   (2) subjecting the fragments to dephosphorylation and end repairing reactions;
   (3) ligating a 5' adaptor A sequence to the fragments, wherein the 5' adaptor A sequence comprise a strand with 5' end phosphorylation modification and the other strand with 3' end dideoxy modification and uracil (U) base sites;
   (4) performing a one-step reaction of Uracil-Specific Excision Reagent enzyme digestion and phosphorylation using Uracil-Specific Excision Reagent (USER) enzyme and T4 polynucleotide kinase;
   (5) ligating a first 3' L-type adaptor sequence to the 5' end of each strand of the phosphorylated nucleic acid fragments;
   (6) performing a first polymerase chain reaction (PCR) amplification to obtain first products having the first adaptor sequence at both ends, wherein the primer sequences used in the first PCR have a U base site and have a nickase recognition sequence, and one of the primers has a biotin label; followed by purification using magnetic beads;
   (7) digesting the first products with a Uracil-Specific Excision Reagent (USER) enzyme to remove the U base site in the primer sequences to generate sticky ends and generate or do not generate a gap;
   (8) performing a double-stranded cyclization of the digested first products to generate cyclic nucleic acid molecules, which having a nickase recognition sequence on one strand and a gap on the other strand or having a nickase recognition sequence but not a gap on both strands, such that cyclization occurs due to the complementarity of the sticky ends to generate cyclized nucleic acid molecules;
   (9) performing linear digestion by treating the cyclic nucleic acid molecules having a nickase recognition sequence on one strand and a gap on the other strand or having a nickase recognition sequence but not a gap on both strands with a nickase to generate a nick;
   (10) performing magnetic purification by binding the treated cyclic nucleic acid molecules to streptavidin magnetic beads via the biotin label on the cyclic nucleic acid molecules; and allowing a solid phase carrier harboring a second affinity label to bind to the cyclic nucleic acid molecules;
   (11) enzymatically digesting the nickase recognition sequence with nickase to get a nick on each single-strand to provide an initiation site for controlled nick translation (CNT), wherein the enzymatic reaction proceeds on the magnetic beads without eluting the nucleic acids from the magnetic beads;
   (12) initiating a controlled nick translation reaction from the nick and/or gap by using the cyclic nucleic acid molecules bound to the streptavidin magnetic beads, wherein in the controlled gap translation reaction, the length of the gap translation fragments generated is controlled by controlling at least one factor selected from the group consisting of the molar ratio of deoxynucleotide triphosphates (dNTPs) to the nucleic acid molecules as template, the enzymatic reaction temperature, and the enzymatic reaction time, to generate nucleic acid fragments with a length in the range of 50-250 base pairs (bp);
   (13) digesting and removing the portion of the respective cyclic nucleic acid molecules that does not undergo the controlled gap translation reaction to obtain linear nucleic acid molecules;
   (14) ligating a second adaptor sequence bubble-type adaptor comprising a top strand and a bottom strand which are complementary to one another to both ends of the linear nucleic acid molecules, wherein the bottom strand having U base sites;
   (15) performing Uracil-Specific Excision Reagent (USER) enzyme digestion of the U base site;
   (16) performing a second polymerase chain reaction amplification to obtain second products having the second adaptor sequence at both ends;
   (17) denaturing the second products to obtain single-stranded nucleic acid molecules, and cyclizing one of the single-stranded nucleic acid molecules with a mediating sequence complementary to both ends of the single-stranded nucleic acid molecule to obtain the library of single-stranded cyclic nucleic acid fragments having double adaptors to produce nucleic acid fragments in a size range of 50 bp to 250 bp, and wherein the steps of the method provide fragments suitable for next-generation sequencing on a Complete Genomics sequencing platform.

2. The method according to claim 1, wherein the first adaptor sequence comprises a first 5' adaptor sequence and a first 3' L-type adaptor sequence that respectively ligate to the 3' end and the 5' end of each strand of the fragments; the first 5' adaptor sequence comprises a 5' end-phosphorylated long strand and a complementary short strand, the short strand having dideoxy modification at the 3' end, and the short strand comprising a U base site; and a portion of the first 3' L-type adaptor sequence which is adjacent to the ligated fragment is complementary to part of the bases of the first 5' adaptor sequence; and
   said ligating a first adaptor sequence to both ends of the nucleic acid fragments specifically comprises:
      dephosphorylating the nucleic acid fragments;
      subjecting the dephosphorylated nucleic acid fragments to end repairing;
      ligating the first 5' adaptor sequence to the 3' end of each strand of the nucleic acid fragments;
      digesting the U base site of the short strand of the first 5' adaptor sequence with a USER enzyme;
      phosphorylating the USER enzyme-digested nucleic acid fragments; and
      ligating the first 3' L-type adaptor sequence to the 5' end of each strand of the phosphorylated nucleic acid fragments.

3. The method according to claim 1, wherein each of the primer sequences used in the first PCR has a U base site and a nickase recognition sequence; and after digesting the U base site with the USER enzyme, sticky ends are formed at both ends of the nucleic acid fragments, and cyclization occurs due to the complementarity of the sticky ends, generating cyclized nucleic acid molecules; then a nickase is used to digest the nickase recognition sequence to generate a nick.

4. The method according to claim 1, wherein one of the primer sequences used in the first PCR has two U base sites, while the other primer sequence has a single U base site; and after digesting the U base sites with the USER enzyme, sticky ends are formed at both ends of the nucleic acid fragments, and cyclization occurs due to the complementarity of the sticky ends, generating cyclized nucleic acid molecules.

5. The method according to claim 4, wherein following cyclizing the digested first products, the method further comprises: digesting the nucleic acid molecules that are not cyclized.

6. The method according to claim 4, wherein said digesting and removing the portion of the respective cyclic nucleic acid molecules that does not undergo the controlled gap translation reaction specifically comprises: first degrading the cyclic nucleic acid molecules with a double strand exonuclease until the gaps at both ends meet; and then degrading the resulting single strands with a single strand exonuclease; or directly excising the portion of the respective cyclic nucleic acid molecules that does not undergo the controlled gap translation reaction with an endonuclease.

7. The method according to claim 4, wherein the second adaptor sequence is a bubble-type adaptor sequence, comprising two base sequences which are complementary to each other in terminal portions but not complementary to each other in a middle portion, thus forming a bubble shape in the middle portion; the middle portion harbors a U base site, and one of the strands of the bubble-type adaptor sequence has an overhanging thymine (T base) at the 5' end; and
    said ligating a second adaptor sequence to both ends of the linear nucleic acid molecules specifically comprises:
    subjecting the linear nucleic acid molecules to end repairing and to a reaction of adding adenine (A base) to the 3' end;
    ligating a bubble-type adaptor sequence to each end of the linear nucleic acid molecules by means of pairing of the T base with the A base; and
    digesting the U base site in the middle portion by using a USER enzyme.

8. The method according to claim 4, wherein following cyclizing the single-stranded nucleic acid molecules, the method further comprises: digesting the single-stranded nucleic acid molecules that are not cyclized.

9. A method for constructing a library of single-stranded cyclic nucleic acid fragments having double adaptors, comprising the following steps in the following order:
    (1) disrupting of 1 μg of genomic DNA using ultrasound in a 96-well polymerase chain reaction (PCR) plate;
    (2) selecting nucleic acid fragments by adding magnetic beads to the disrupted DNA and separating the beads on a magnetic rack;
    (3) dephosphorylation of the fragments using shrimp alkaline phosphatase;
    (4) end-repairing the fragments using deoxyribonucleotide triphosphates (dNTPs), bovine serum albumin and T4 deoxyribonucleic acid polymerase;
    (5) ligating a 5' adaptor A sequence using having SEQ ID NO: 1 and a 5' blocking sequence having SEQ ID NO: 2;
    (6) digesting the products of step (5) in a one-step reaction with Uracil-Specific Excision Reagent (USER) enzyme and phosphorylation using T4 polynucleotide kinase;
    (7) ligating a first adaptor 3' L-type adaptor A sequence having SEQ ID NO: 3 using T4 DNA ligase;
    (8) performing a first polymerase chain reaction (PCR) using primer 1 having SEQ ID NO: 4 and primer 2 having SEQ ID NO: 5 followed by purification using magnetic beads;
    (9) removal of uracil using USER enzyme;
    (10) double strand cyclization;
    (11) linear digestion followed by magnetic purification, wherein the initiation site is in the form of a nick, and adaptor A sequence harbors and a nickase recognition sequence;
    (12) binding cyclic DNA to streptavidin magnetic beads which bind via a biotin label on the DNA;
    (13) enzymatic digestion with nickase;
    (14) controlled gap translation reaction using dNTPs and DNA polymerase I;
    (15) digestion at the gap by T7 endonuclease I;
    (16) filling of sticky ends and addition of A at the 3' end using Klenow fragment and Klex NTA mix;
    (17) ligation of a bubble-type adaptor comprising a top strand and a bottom strand, which are complementary to one another having SEQ ID NO: 6 and SEQ ID NO: 7;
    (18) USER enzyme digestion;
    (19) performing polymerase chain reaction using primer F and primer R having SEQ ID NO: 8 and SEQ ID NO: 9;
    (20) single strand cyclization by nucleic acid single strand O via corresponding complementary sequences, wherein the nucleic acid single strand O having SEQ ID NO: 10; and
    (21) linear DNA digestion using Exonuclease 1 and Exonuclease 3, to produce nucleic acid fragments in a size range of 200 bp to 300 bp, and wherein the steps of the method provide fragments suitable for next-generation sequencing on a Complete Genomics sequencing platform.

* * * * *